United States Patent [19]

Modrovich

[11] 4,310,624

[45] * Jan. 12, 1982

[54] STABILIZED LIQUID COENZYME COMPOSITIONS FOR DIAGNOSTIC DETERMINATIONS

[76] Inventor: Ivan E. Modrovich, 1043 Mesa Dr., Camarillo, Calif. 93010

[*] Notice: The portion of the term of this patent subsequent to May 8, 1996, has been disclaimed.

[21] Appl. No.: 775,833

[22] Filed: Mar. 9, 1977

Related U.S. Application Data

[63] Continuation-in-part of Ser. No. 764,826, Feb. 2, 1977, Pat. No. 4,153,511, which is a continuation of Ser. No. 667,857, Mar. 17, 1976, abandoned.

[51] Int. Cl.³ .................... C12Q 1/00; C12Q 1/32; C12Q 1/48; C12N 9/00
[52] U.S. Cl. .................................. 435/4; 435/14; 435/16; 435/17; 435/26; 435/183
[58] Field of Search ............... 195/99, 101, 103.5 R; 536/28; 435/4, 14, 15, 16, 17, 26, 188, 183

[56] References Cited

U.S. PATENT DOCUMENTS 2,882,244  4/1959  Milton ........................... 252/455 Z
3,776,900 12/1973  Hammer ............................ 536/28
3,819,487  6/1974  Bernt et al. .................. 195/103.5 R

FOREIGN PATENT DOCUMENTS 2615958 12/1976 Fed. Rep. of Germany.

OTHER PUBLICATIONS

George et al., Biochim. Biophys. Acta. 191 (1969), pp. 466–468.

*Primary Examiner*—David M. Naff
*Attorney, Agent, or Firm*—Robert J. Schaap

[57] ABSTRACT

Labile coenzymes, such as reduced nicotinamide-adenide dinucleotide ($NADH_2$), used in biological diagnostic determinations are stabilized by forming a composition of the coenzyme with an organic solvent such as 1,2 propanediol in the presence of at least 1% by volume of a solid, inert hygroscopic agent such as 10% by volume of a molecular sieve material. After stabilization, the inert hygroscopic agent can be removed without materially affecting stabilization of the composition. The stabilized composition shows excellent shelf life and a container in which the composition is stored may be repeatedly opened for use without degradation of the labile coenzymes such as the labile $NADH_2$.

20 Claims, No Drawings

STABILIZED LIQUID COENZYME COMPOSITIONS FOR DIAGNOSTIC DETERMINATIONS

RELATED APPLICATIONS

This application is a continuation-in-part of application Ser. No. 764,826, filed Feb. 2, 1977, now U.S. Pat. No. 4,153,511, for STABILIZED LIQUID COENZYME COMPOSITIONS and which is in turn a continuation of Application Ser. No. 667,857, filed Mar. 17, 1976, now abandoned, for STABILIZED LIQUID COENZYME COMPOSITIONS.

BACKGROUND OF THE INVENTION

I. Field of the Invention

This invention relates in general to certain new and useful improvements in the stabilization of coenzymes and the method of stabilizing, and, more particularly, to stabilized labile coenzymes in a single aqueous organic solvent media.

II. Description of the Prior Art

It has recently been estimated that 25% of all in vitro diagnostic tests conducted annually in this country are not reliable. Unreliable tests can result in unnecessary medical treatment, the withholding of necessary treatment and lost income. Because of their high specificity, the use of enzyme determinations has significantly increased during the last few years and indications are that this trend will continue. However, rigorous quality control measures are required to assure the accuracy and consistency of results. This requirement stems from the fact that the exact nature of enzymes, as well as the mechanisms of their action, remains unknown for the most part.

At present, the greatest limitation on the enzyme reagent manufacturer, by far, lies in the unstable characteristics of his products. Current methodologies require the use of numerous labile ingredients, and these ingredients are more likely to increase, rather than decrease, in number. Due to these severe restraints, rigorous quality control is required, and this quality control is, of course, costly. Moreover, if control in any step in the process is not maintained within high degree of control standards, the quality of the final product can be reduced materially.

The present commercial state of the art used for stabilizing the reactive ability of enzymes or coenzymes is by locking them into a solid matrix either by freeze drying, dry blending, such as used for tableting dried powders, primarily in the pharmaceutical diagnostic and related industries and immobilization by locking the chemical structure of the enzyme into a solid matrix. Contrary to the sophistication these terms imply, these approaches are neither practical nor desirable and are also expensive. The manufacturer is forced to remove the water and supply a partial product, thus relinquishing part of the quality control cycle in the dilution and use of the final product. Laboratories are forced to pay the high cost of packaging, reagent waste, freeze drying and dry blending, and usefulness of the product is further limited by packaging modes and sizes.

Furthermore, good product uniformity is difficult to achieve. This condition is exemplified by the fact that most commercial freeze dried control sera (reference serum) list the acceptable bottle-to-bottle variation of enzyme constituents at ±10% of the mean.

OBJECTS OF THE INVENTION

It is, therefore, the primary object of the present invention to provide a liquid stabilized coenzyme composition which is stabilized in the presence of an organic solvent.

It is an additional object of the present invention to provide a liquid stabilized coenzyme composition of the type stated in a single container which has excellent shelf life and which container may be repeatedly opened without substantial degradation of the labile components therein.

It is another object of the present invention to provide a labile coenzyme composition of the type stated which may be stored in a liquid media, in the presence of another coenzyme and/or other labile enzymes or substrates and all of which are stabilized against degradation.

It is a further object of the present invention to provide a liquid stabilized labile coenzyme composition of the type stated and where the stabilization of the enzyme does not affect the enzymatic reactivity after a substantial period of time.

It is also an object of the present invention to provide a method of stabilizing labile coenzymes in a liquid media with relatively low-cost, commercially available stabilizing ingredients.

With the above and other objects in view, my invention resides in the novel features of form and combination of components as presently described.

SUMMARY OF THE DISCLOSURE

In the clinical diagnostic field, the commercial application is represented by, but not limited to, the diagnostic reagents used to determine and quantitate the following constituents in biological fluids:

1. Glutamic-oxalacetic transaminase (SGOT);
2. Glutamic-pyruvic transaminase (SGPT);
3. Lactic dehydrogenase (LDH);
4. Creatine Phosphokinase (CPK);
5. α-Hydroxybuteric dehydrogenase (α-HBD)
6. Glucose (via Hexokinase and G-6-PDH). These reagents react similarly, contain some common labile ingredients, and some of the chemical reactions involved are common. The following chemical reaction scheme is presented as a model to illustrate the general nature of the reactions involved:

REACTION SCHEME 1. - GENERAL MODEL

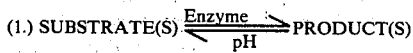

(1.) SUBSTRATE(S) $\underset{pH}{\overset{Enzyme}{\rightleftharpoons}}$ PRODUCT(S)

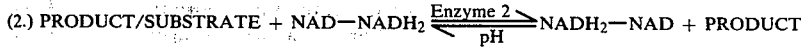

(2.) PRODUCT/SUBSTRATE + NAD—NADH$_2$ $\underset{pH}{\overset{Enzyme\ 2}{\rightleftharpoons}}$ NADH$_2$—NAD + PRODUCT

REACTION SCHEME 1. - GENERAL MODEL (3.) NADH$_2$ + CHROMOGEN $\underset{}{\overset{\text{Catalyst}}{\rightleftharpoons}}$ CHROMOGEN + NAD
        (oxidized)                             (reduced)

All enzymatic reactions listed above will follow this general scheme, where reaction (2.) is usually referred to as the coupling reaction, reactions (2.) or (3.) are the measuring reactions, and reaction (1.) may be characterized as the primary reaction. It is understood however, that not all three reactions are required for measurement; in fact, they may be limited to two, or one. In the case of the ultraviolet measurement of lactic dehydrogenase (LD) activity, only reaction (2.) is involved, as follows:

REACTION SCHEME 2. - LDH

Pyruvate + NADH$_2$ $\underset{}{\overset{\text{LDH}}{\rightleftharpoons}}$ NAD + Lactate Conversely, more than the three reactions listed may be involved as is the case in the colorimetric determination of Creatine phosphokinase (CPK):

REACTION SCHEME 3. - CPK (1.) CP + ADP $\underset{}{\overset{\text{CPK}}{\rightleftharpoons}}$ ATP + Creatine (2.) ATP + Glucose $\underset{}{\overset{\text{HK}}{\rightleftharpoons}}$ Glucose-6-Phos. + ADP (3.) Glucose-6-Phos. + NAD $\underset{}{\overset{\text{G-6-PDH}}{\rightleftharpoons}}$ NADH$_2$ (4.) NADH$_2$ + INT $\underset{}{\overset{\text{PMS}}{\rightleftharpoons}}$ INT + NAD
                (ox)      (red)

SYMBOLS:
CP = Creatine phosphate
ADP = Adenosine-5'-diphosphate
ATP = Adenosine triphosphate
HK = Hexokinase
NAD = Nicotinamide-adenine dinucleotide
NADH$_2$ = Nicotinamide-adenine dinucleotide, reduced
NADPH = Nicotinamide-adenine dinucleotide phosphate, reduced
G-6-PDH = Glucose-6-phosphate dehydrogenase
INT = tetrazolium salt
PMS = phenazine methosulfate In this case, reactions (2.) and (3.) may be considered the coupling reactions, reactions (3.) or (4.) the measuring reactions, and reaction (1.) the primary reaction.

Referring to REACTION SCHEME L,—GENERAL MODEL, it becomes obvious and is general knowledge that the use of the reaction sequence permits the analytical quantitation of either the reaction substrates/products or the catalyzing enzymes.

The quantitation of these constituents in biological fluids is a well accepted and widely used diagnostic tool in diagnosis and treatment of human and animal disease states.

Enzymes are large molecular weight, complex protein molecules, usually as yet unknown chemical structure. They are presently classified by their catalytic activity and extreme substrate specificity. Enzymes may be redefined as biological catalysts, capable of catalyzing a reaction of a single substrate, or a reaction of a similar group of substrates.

Coenzymes are lower molecular weight organic chemicals of well-defined structure, whose reactions or interactions are necessary for specific enzyme assay or reaction. They are catalyzed resulting in an irreversible change in the coenzyme's structure and/or atomic composition. Coenzymes are very useful in clinical assay procedure. Some have strong absorbance, their reactions are stoichiometric with the substrate and therefore the creation or disappearance of the absorbing form can be followed photometrically. Nicotinamide adenide dinucleotide (NAD) and its reduced form (NADH$_2$) are used in many important clinical assays such as the SGOT, SPGT and LDH assays previously described. NAD and NADH$_2$ and their salts have a molecular weight of about 700 and are very complex organic molecules. NADH$_2$ absorbs strongly at 340 nm whereas NAD does not absorb at this wavelength.

NADH$_2$ is extremely unstable in water solution or in dry form when exposed to humid environments. Even when frozen NADH$_2$ must be kept free of moisture. Stability is better at alkaline pH, whereas at acid pH, NADH$_2$ decomposes very rapidly in a matter of minutes. Neither the exact mechanism, nor the end products are of significance except that decomposed NADH$_2$ can no longer effectively function as a coenzyme nor does it possess the extinction coefficient at 340 nm. The typical commercial form is a dry dessicated package or freeze dried stored under nitrogen.

Labile coenzymes are treated according to the invention resulting in long term stability without affecting coenzymatic reactivity or photometric absorptivity. The invention provides reagents where quality control is assured throughout manufacturing, packaging, storage and use. The inconvenience of rigid package size is eliminated as is the high cost of packaging, freeze drying and reagent waste. Liquid enzyme and coenzyme systems provide application flexibility and separation of the ingredients is easily accomplished with negligible manufacturing cost providing the flexibility of triggering the desired reaction after all side reactions have been dissipated.

The stabilized coenzymes of the invention have been assessed in studies which compared liquid coenzyme reagents with fresh reagents. The studies show a 1:1 correlation between aged liquid and fresh reagents with comparable sensitivity and precision. Providing coenzyme reagents in a stable liquid form enhances the colorimetric applicability of present day NAD/NADH coupled methodologies primarily because the separation of ingredients is easily accomplished. NADPH has also been found to be effective in the present invention. Stable liquid reagents are especially advantageous where NADH consumption is the basis of measurement and the color reagent must be separated from NADH and the reaction main. In the ultraviolet mode, the liquid system offers better reagent homogeneity and packaging, as well as flexibility in usage, in contrast to the freeze-dried or dry media preparations.

In diagnostic enzymology, the stabilization of enzyme reagents in a ready-to-use liquid media is a new and exciting approach to satisfy the needs of the clinical laboratory and the reliability demands of the regulatory authorities. The flexibility of liquid enzyme systems insures their applicability to automated instrumentation, as well as their convenience in manual testings.

Stabilization of labile coenzymes is accomplished in accordance with the invention by dissolving the coenzymes in an organic solvent. After solution is achieved, at least 1% V/V of inert hygroscopic solid is added and the container closed. The suspension is maintained at room temperature at least 1 hour, usually 1 to 2 days, with occasional mixing to remove water from the mixture down to a level of no more than 0.5%. The solution may then be dispensed into amber-glass bottles. After this period of time, the 1% V/V hygroscopic agent is removed from the suspension, conveniently by pouring or dispensing small quantities of the liquid into another container and thus filtering out the hygroscopic agent, and which container is sealed airtight and stored under refrigeration. Projected shelf life is up to 4 years under these conditions without appreciable degradation.

Surprisingly, the coenzyme $NADH_2$ exhibits good solubility and stability in the aqueous miscible organic solvent even though solvents such as 1,2-propanediol are hygroscopic. Evidently, the solvent molecules efficiently solvate the coenzyme protecting it from water and the solvent media acts as an efficient transfer media, delivering the absorbed water to the solid hygroscopic agent where it is irreversibly bound. Even after removal of the hygroscopic agent, it has been found that additional amount of water entrainment after opening the container is relatively small so that it does not materially affect degradation of the composition.

These and many other features and attendant advantages of the invention will become apparent as the invention becomes better understood by reference to the following detailed description.

DESCRIPTION OF THE PREFERRED EMBODIMENTS

The organic solvent should have the following characteristics:
1. Low water content (trace <0.1%):
2. Neutral or alkaline pH;
3. Liquid at room temperatures and preferably room and refrigerator temperatures;
4. Does not react with $NADH_2$ other than forming electrostatic (i.e., hydrogen) bonds;
5. Miscible with water;
6. Standard free energy of solvolysis is low (normal resonance is established).

Non-reactive organic solvents of neutral or alkaline pH, such as alcohols, especially liquid polvols containing from 2-4 hydroxyl groups and 2-10 carbon atoms, are preferred, such as glycerol, ethylene glycol, propylene glycol or butane diol. Propylene glycol, 1,2-propanediol, was found to possess all these qualities and is the solvent of choice.

The inert hygroscopic solid maintains the desired low water content, i.e., below 0.5%, preferably below 0.1%. The hygroscopic solid must be an efficient water absorber nonreactive with the coenzyme and of neutral or alkaline pH. The solid is preferably a high area hygroscopic agent such as a natural or synthetic molecular sieve having a particle size from 2-16 mesh present in an amount of at least 1% V/V, typically from 5-20% V/V. The amount of surface area is important since the material acts to absorb water into the pores.

Molecular sieves are zeolites or similar materials whose atoms are arranged in a crystal lattice in such a way that there are a large number of small cavities interconnected by smaller openings or pores of precisely uniform size. Normally, these cavities contain water molecules, but, upon heating under vacuum, this water is driven off without any change in the remaining crystal lattice. The network of cavities and pores may occupy 50% of the total volume of the crystals. Molecular sieves have a strong tendency to reabsorb water, and other small molecular weight liquids.

A few natural zeolites exhibit molecular sieve characteristics to a limited degree. Synthetic ziolites are available in several sizes (pore openings 3, 4, 5 and 10 angstrom units in diameter) with high capacity for absorption and regeneration even when used at elevated temperatures.

It has been found in connection with the present invention that after the composition has been stabilized in the presence of the organic solvent as well as the inert hygroscopic solid, the hydroscopic solid may be removed without otherwise materially affecting the stability of the composition. Generally, it has been found that the composition should be stored for a period of at least about 24 hours at room temperature in the presence of the hygroscopic solid. During this time, any trace of water has been absorbed by the hygroscopic solid and, upon removal of the same, there is essentially no water available in the composition. The composition may also be opened on a limited basis and even though entrained water in the air may enter the upper end of the container, the amount of water is relatively small so that it does not cause any material decomposition of the labile components in the composition.

Generally, the hygroscopic solid should be kept in contact with the stabilized solution for a period which depends upon the amount of water which was initially in the solution at the time of preparation. In many cases, it has been found that the hygroscopic solid should remain in contact with the solution for about three to four days. This time can be shortened by heating the composition at least to the point where no decomposition of the labile components will occur. Thus, it has been found that it is possible to heat the compositions to about a 60° C. temperature without affecting the labile components. The important factor is that the hygroscopic solid should remain in the solution until there is no more than about 0.5% V/V of water.

In the aforementioned parent patent application Ser. No. 667,857, filed Mar. 17, 1976, it was deemed necessary to maintain the hygroscopic solid along with the organic solvent in the composition in order to maintain stability. However, it has been subsequently found that stability of the composition is not materially decreased even when the hygroscopic solid has been removed after the initial stage of stability has been attained.

The composition of the present invention which has been stabilized may be introduced into containers of proper size for purposes of determination of body components. By removal of the hygroscopic agent, it is now possible to dispense precise and accurate quantities due to the fact that the hygroscopic agent would otherwise absorb some of the solvent itself, or at least maintain a portion of the solvent on the surface of the hygroscopic agent by surface tension. In this way, it is now possible to dispense precise amounts in those cases where quantitization of the solution is a critical or important factor.

For example, it can be observed that the coefficient of expansion of some of the solvents, as for example propylene glycol is temperature dependent. The amount of the solution which can be dispensed into a container can be very carefully controlled at the manufacturing site, but is not easily controlled in the field during use.

In the prior art, freeze-dried compositions have been provided and these compositions required dilution with water for further use in determinations. However, while a container of composition of the present invention may require dilution with water for purposes of determination, it has been found that the degree of error which might otherwise be introduced is substantially less than the prior art freeze-dried compositions which were diluted. For example, considering a freeze-dried composition which is diluted with water, it has been found that any error in the amount of water with respect to the freeze-dried composition is approximately ten times the amount of error with respect to the ratio of the components when compared to a like dilution factor in the composition of the present invention. Hence, Applicant has found that it is possible to provide a container which can be easily diluted without substantially increasing the error rate in any determination.

It has also been found in accordance with the present invention that the compositions described herein may also be stabilized in the presence of other labile components other than the enzymes, as described above. Thus, for example, the stabilized composition may also include coenzymes, as for example NAD and NADH, etc., or the various substrates which are compatible with the compositions. In each case, it has been found that the substrates and the coenzymes are stabilized in accordance with the present invention along with the specifically described enzymes herein.

The coenzyme can be present up to its solubility limit and is preferably as concentrated as possible since propylene glycol is an enzyme inhibitor and can interfere with the primary or coupling enzymatic activity if too much is carried into the test from the coenzyme reagent. Typical $NADH_2$ compositions according to the invention contain about 2–15 g/l, typically about 7 g/l. Hydrated $NADH_2$ can also be utilized for speedier solution in the polyol solvent.

EXAMPLES

The invention is further illustrated by, but not limited to the following Examples.

EXAMPLE 1

6.65 g/l of $NADH_2$ was dissolved in spectroquality 1,2 propanediol in a closed amber glass container. After complete solution is attained, 10% V/V of molecular sieves (4 mesh) were added and the container was closed and left at room temperature for 24 hours with occasional mixing to reduce water in the mixture below 0.01%. The solution was dispensed into final marketing amber-glass bottles containing fresh 4-mesh molecular sieves (10% V/V). The containers were sealed airtight and stored under refrigeration. An Arrhenius plot depicting the temperature stability profile of $NADH_2$ degradation in this media indicates storage stability of up to 4 years without significant degradation. The data was obtained at three storage temperatures of 60° C., room temperature (~25° C.), and at refrigerated temperatures of ~ −8° C. (The mean of 4° C. was used.) The maximum allowable loss is less than 10% after 360 days storage at 27° C.

When propylene glycol is utilized without first stabilizing in the presence of the hygroscopic agent and removal thereafter, the $NADH_2$ degrades quite quickly in use when subject to opening and closing the container.

In the preceding Example 1, the molecular sieves were retained in the final composition as stored. In the following Example 2, the molecular sieves were removed after stabilization of the composition has been achieved and were not included in the sealed containers. Nevertheless, the stability of the composition was not materially affected.

EXAMPLE 2

6.65 g/l of $NADH_2$ was dissolved in spectroquality 1,2 propanediol in a closed amber glass container. After complete solution is attained, 10% V/V of molecular sieves (4 mesh) were added and the container was closed and left at room temperature for 24 hours with occasional mixing to reduce water in the mixture below 0.01%. The supernate solution was dispensed into final marketing clear glass vials. The containers were sealed airtight and stored under refrigeration. An Arrhenius plot depicting the temperature stability profile of $NADH_2$ degradation in this media also indicates storage stability of up to 4 years without significant degradation. The data was obtained at three storage temperatures of 40° C., room temperature (~25° C.), and at refrigerated temperatures of 2°–8° C. (The mean of 4° C. was used.) The maximum allowable loss is less than 10% after 360 days storage in the dark at 27° C.

Again, when the propylene glycol is utilized without first stabilizing in the presence of the hygroscopic agent, $NADH_2$ degrades quite quickly in use when subject to opening and closing the container.

EXAMPLE 3

The composition of Example 2 after removal of the excess water by means of the hygroscopic solid is then dispensed into single test clear glass vials along with a coenzyme, NADH, in the amount of 20 microliters per vial. A tight-fitting screw-type cap was placed on the open upper end of these vials. These vials are highly effective for use in single determinations of SGOT, SGPT, LBDH and LDH-P, merely by adding the corresponding appropriate substrate thereto.

It is to be realized that only preferred embodiments of the invention have been described and that numerous substitutions, modifications and alterations are permissible without departing from the spirit and scope of the invention as defined in the following claims.

Having thus described my invention, what I desire to claim and secure by Letters Patent is:

1. A method of stabilizing a labile coenzyme used in biological diagnostic determinations and which coenzyme is normally unstable in aqueous media, said method comprising the steps of:
   dissolving the coenzyme in a non-reactive, water-miscible, organic solvent which is liquid at least at room temperatures to form a solution thereof, said coenzyme cooperating with and affecting reactivity of an enzyme in a biological diagnostic determination;
   adding at least 1% of an inert hygroscopic solid to the solution to form a suspension;
   stirring the suspension and entrapping water with the hygroscopic solid so that the residual water content is below 0.5% and where activity of the coenzyme remains unaffected by the presence of the organic solvent in the stabilized composition or in a biological diagnostic determination reaction; removing the hygroscopic solid from the suspension;

and sealing the solvent with said coenzyme dissolved therein.

2. The method according to claim 1 in which the coenzyme is present in the organic solvent which is liquid at room and refrigerator temperatures.

3. The method according to claim 1 in which the hygroscopic solid is a high surface area, particulate hygroscopic solid.

4. A method according to claim 1 in which the coenzyme is selected from $NADH_2$ or hydrated $NADH_2$.

5. A method according to claim 4 in which the concentration of $NADH_2$ is above 2 g/l.

6. A method according to claim 4 in which the solvent has the following characteristics:
 1. Low water content (trace <0.1%);
 2. Neutral or alkaline pH;
 3. Liquid at room and refrigerator temperatures;
 4. Does not react with $NADH_2$ other than forming electrostatic (i.e., hydrogen) bonds;
 5. Miscible with water;
 6. Standard free energy of solvolysis is low (normal resonance is established).

7. A method according to claim 6 in which the solvent is a polyol containing 2-4 hydroxyl groups and 2-10 carbon atoms.

8. A method according to claim 7 in which the solvent is 1,2-propane diol.

9. A method according to claim 8 in which the solvent with said coenzyme dissolved therein contains no more than 0.1% water before sealing.

10. A method according to claim 9 in which the inert hygroscopic solid is a molecular sieve present in an amount from 5-20% V/V.

11. A method according to claim 10 in which the molecular sieve has a particle size from about 2-16 mesh.

12. A method according to claim 1 in which the solvent with said coenzyme dissolved therein is sealed in a container in a liquid stage in amounts required for direct analysis.

13. A method according to claim 1 in which the coenzyme is selected from $NADH_2$ ot hydrated $NADH_2$ or NADPH.

14. A method of stabilizing a labile coenzyme used in biological diagnostic determinations and which coenzyme is normally unstable in aqueous media, said method comprising the steps of:

dissolving the coenzyme in an amount near or at its solubility limit in a non-reactive, water-miscible polyol which is liquid at least at room temperatures to form a solution thereof, said coenzyme cooperating with and affecting reactivity of an enzyme in a biological diagnostic determination, said polyol containing 2-4 hydroxyl groups and 2-10 carbon atoms and having the following characteristics:
 1. Low water content (trace 0.1%),
 2. Neutral or alkaline pH,
 3. Liquid at room and refrigerator temperatures,
 4. Does not react with the coenzyme other than forming electrostatic (i.e. hydrogen) bonds,
 5. Miscible with water,
 6. Standard free energy of solvolysis is low (normal resonance is established);

adding at least 1% of an inert high surface area, particulate hygroscopic solid to the polyol-coenzyme solution to form a suspension;

stirring the suspension and entrapping water with the hygroscopic solid so that the residual water content is below 0.5% and where activity of the coenzyme remains unaffected by the presence of the polyol in the stabilized composition or in a biological diagnostic determination reaction;

removing the hygroscopic solid from the suspension; and sealing the solvent with said coenzyme dissolved therein in a container in an amount required for direct analysis.

15. A method according to claim 14 in which the coenzyme is selected from $NADH_2$ or hydrated $NADH_2$.

16. A method according to claim 15 in which the concentration of $NADH_2$ is above 2 g/l.

17. A method according to claim 16 in which the solvent is 1,2-propane diol.

18. A method according to claim 17 in which the inert hygroscopic solid is a molecular sieve present in an amount from 5-20% V/V and has a particle size from about 2-16 mesh.

19. A method according to claim 18 in which the solvent with said coenzyme dissolved therein contains no more than 0.1% water before sealing.

20. A method according to claim 14 in which the coenzyme is selected from $NADH_2$ or hydrated $NADH_2$ or NADPH.

* * * * *